United States Patent
Berger et al.

(12)

(10) Patent No.: US 6,428,702 B1
(45) Date of Patent: Aug. 6, 2002

(54) METHOD OF SAMPLE INTRODUCTION FOR SUPERCRITICAL FLUID CHROMATOGRAPHY SYSTEMS

(75) Inventors: Terry A. Berger, Newark; Kimber D. Fogelman, Hockessin, both of DE (US)

(73) Assignee: Berger Instruments, Inc., Newark, DE (US)

( * ) Notice: Subject to any disclaimer, the term of this patent is extended or adjusted under 35 U.S.C. 154(b) by 0 days.

(21) Appl. No.: 09/918,435

(22) Filed: Aug. 1, 2001

(51) Int. Cl.$^7$ ............................................... B01D 11/00
(52) U.S. Cl. ...................... 210/634; 73/61.56; 210/136; 210/656; 422/69; 422/103; 436/161
(58) Field of Search ............................... 210/136, 198.2, 210/511, 541, 634, 656; 96/101, 105, 106; 422/70, 103, 6; 73/23.34, 23.41, 23.42, 61.52, 61.56, 61.59; 436/161, 174, 180

(56) References Cited

U.S. PATENT DOCUMENTS

| | | | | |
|---|---|---|---|---|
| 4,734,190 A | * | 3/1988 | Fulton et al. | 210/198.2 |
| 5,198,115 A | * | 3/1993 | Stalling et al. | 210/634 |
| 5,340,475 A | * | 8/1994 | Cortes et al. | 210/198.2 |
| 5,866,004 A | * | 2/1999 | Houck et al. | 210/634 |
| 6,260,407 B1 | * | 7/2001 | Petro et al. | 210/198.2 |

* cited by examiner

Primary Examiner—Joseph W. Drodge
(74) Attorney, Agent, or Firm—Joseph J. Zito; Kendal M. Sheets; Zito tlp

(57) ABSTRACT

An improved method and apparatus for safely introducing sample into a flow stream of a supercritical fluid chromatography system is described. The sample injection method improves safety of injection by eliminating the risk of injecting sample into a high-pressure system containing liquids and gasses at or near supercritical ranges. The method improves the efficiency and significantly shortens the time of the injection process by using a check valve placed between a fill port on an injection valve and sample port where sample is injected by a syringe. After sample injection from a sample loop into a high-pressure flow stream, an injection valve is reset to receive a subsequent sample. High-pressure flow stream mixtures become trapped within the sample loop when the valve is reset. The check valve prevents the mixtures from expanding into the sample port and blowing out a syringe and flow stream mixtures from the fill lines. The trapped flow stream mixtures are directed to a waste port where they are safely contained. The technique can be applied equally as effective to preparatory SFC as well as to analytical SFC systems.

13 Claims, 4 Drawing Sheets

METHOD OF SAMPLE INTRODUCTION FOR SUPERCRITICAL FLUID CHROMATOGRAPHY SYSTEMS

BACKGROUND OF THE INVENTION

Supercritical fluid chromatography (SFC) has advanced over the past decade. SFC uses highly compressible mobile phases, which typically employ carbon dioxide (CO2) as a principle component. In addition to CO2, the mobile phase frequently contains an organic solvent modifier, which adjusts the polarity of the mobile phase for optimum chromatographic performance. Since different components of a sample may require different levels of organic modifier to elute rapidly, a common technique is to continuously vary the mobile phase composition by linearly increasing the organic modifier content. This technique is called gradient elution.

SFC has been proven to have superior speed and resolving power compared to traditional HPLC for analytical applications. This results from the dramatically improved diffusion rates of solutes in SFC mobile phases compared to HPLC mobile phases. Separations have been accomplished as much as an order of magnitude faster using SFC instruments compared to HPLC instruments using the same chromatographic column.

SFC instruments used with gradient elution also reequilibrate much more rapidly than corresponding HPLC systems. As a result, they are ready for processing the next sample after a shorter period of time. A common gradient range for gradient SFC methods might occur in the range of 2% to 60% composition of the organic modifier.

It is worth noting that SFC instruments, while designed to operate in regions of temperature and pressure above the critical point of CO2, are typically not restricted from operation well below the critical point. In this lower region, especially when organic modifiers are used, chromatographic behavior remains superior to traditional HPLC and often cannot be distinguished from true supercritical operation.

In analytical SFC, once the separation has been performed and detected, the highly compressed mobile phase is directed through a decompression step to a waste stream. During decompression, the CO2 component of the mobile phase is allowed to expand dramatically and revert to the gas phase. The expansion and subsequent phase change of the CO2 tends to have a dramatic cooling effect on the waste stream components. If care is not taken, solid CO2, known as dry ice, may result and clog the waste stream. To prevent this occurrence, heat is typically added to the flow stream. At the low flow rates of typical analytical systems only a minor amount of heat is required.

While the CO2 component of the SFC mobile phase converts readily to a gaseous state, moderately heated liquid organic modifiers typically remain in a liquid phase. In general, dissolved samples carried through SFC system also remain dissolved in the liquid organic modifier phase.

The principle that simple decompression of the mobile phase in SFC separates the stream into two fractions has great importance with regard to use of the technique in a preparative manner. Removal of the gaseous CO2 phase, which constitutes 50% to 95% of the mobile phase during normal operation, greatly reduces the liquid collection volume for each component and thereby reduces the post-chromatographic processing necessary for recovery of separated components.

Expanding the technique of analytical SFC to allow preparative SFC requires several adaptations to the instrument. First the system requires increased flow capacity. Flows ranging from 20 ml/min to 200 ml/min are suitable for separation of multi-milligram up to gram quantities of materials. Also, a larger separation column is required. Finally, a collection system must be developed that will allow, at a minimum, collection of a single fraction of the flow stream which contains a substantially purified component of interest. In addition, there frequently exists a compelling economic incentive to allow multiple fraction collections from a single extracted sample. The modified system must also be able to be rapidly reinitialized either manually or automatically to allow subsequent sample injection followed by fraction collection.

Sample injection valves in SFC introduce a measured sample into the mobile phase flow stream prior to entering a chromatography column. Common injection valves are fixed-loop multi-port injection valves with either internal or external loops. Direct fill loop injections are a normal means of sample introduction in SFC so that a packed column in SFC has similar quantitative reproducibility to LC using fixed loop injectors.

Injection valves used in SFC sample introduction present special hazards caused by the high pressures found in SFC systems. Sample is manually injected into the sample loop with a syringe through some type of fill port. During an injection, the valve loop has discharges sample contents into a mobile phase flow stream and the valve is returned to a load position. However, mobile phase from the flow stream becomes trapped inside the sample loop. Switching the injection valve loops, loaded with high-pressure mobile phase from the previous injection, back to a load position at ambient laboratory pressure exposes the sample fill port to highly compressed mobile phase inside the loop.

The compressed mobile phase will rapidly expand when exposed to atmospheric pressure. A hazard occurs when mobile phase from a trapped in an injection loop expands back up through an injection system and out into a laboratory. Dissipating this pressure to a waste line also causes greater attention to the injection process and time delays which slows the entire SFC sample processing time. There is a need for a cost-effective solution in an SFC system to prevent high-pressure blowback from a sample injection valve and to minimize time delays associated with venting high-pressure build-up prior to sample injections.

SUMMARY OF THE INVENTION

The present invention is an improved method and apparatus for safely introducing sample into a flow stream of a supercritical fluid chromatography system. The sample injection method described herein improves safety by minimizing risk of exposure to hazardous chemicals in the SFC flow stream caused by blowback of mobile phase through a sample port. The invention also improves the efficiency and significantly shortens the time of the injection process by avoiding the need to dissipate built-up pressure in an injection valve prior to reloading an injection loop.

Samples are normally introduced to an SFC mobile phase flow stream via a syringe, or syringe pump, and a multi-port injection valve. After sample injection from a sample loop into a high-pressure flow stream, an injection valve is reset to load a new sample from a syringe. However, high-pressure flow stream mixtures become trapped within the sample loop when the valve is rotated to load a load position. The trapped flow stream in the valve exists at extreme pressure, up to 600 bar, and can quickly escape from the valve when the loop is opened at atmospheric pressure in the load position. A real hazard occurs when mobile phase flow stream contents explode outside of the injection port and into laboratory air. The flow stream contains highly compresses gasses and solvent modifier, all of which are potentially hazardous chemicals to humans and sensitive laboratory equipment. Aerosols and gasses can blow through a sample fill port and into the atmosphere, endangering laboratory personnel, equipment and the environment. Also, syringes are used in SFC to manually inject sample into an injection valve loop. Syringes are not always removed properly from a fill port after filling an injection loop. The pressure from trapped mobile phase in an injection valve loop from a previous injection can blow a syringe out of the sample fill port and propel the sharp projectile at high velocity through the laboratory.

The present invention is an improvement over SFC sample injection methods by reducing safety concerns in the laboratory and increasing efficiency of injection rates. The method comprises placing a check valve downstream of a sample fill port, where sample is introduced into a line that feeds the injection loop, and the port on injection valve leading to an injection loop. The check valve prevents high-pressure mobile phase trapped in the injection loop from expanding out of a sample fill port. The trapped flow stream mixtures are blocked from the fill port and directed out of an injection valve loop to a waste port, where the mobile phase is safely depressurized and contained. The method of the invention quickly releases pressure in a loop to the waste port and therefore prepares the injection loop for a subsequent sample injection without additional handling or time delays experienced with prior systems.

DETAILED DESCRIPTION OF A PREFERRED EMBODIMENT

Figure 1:
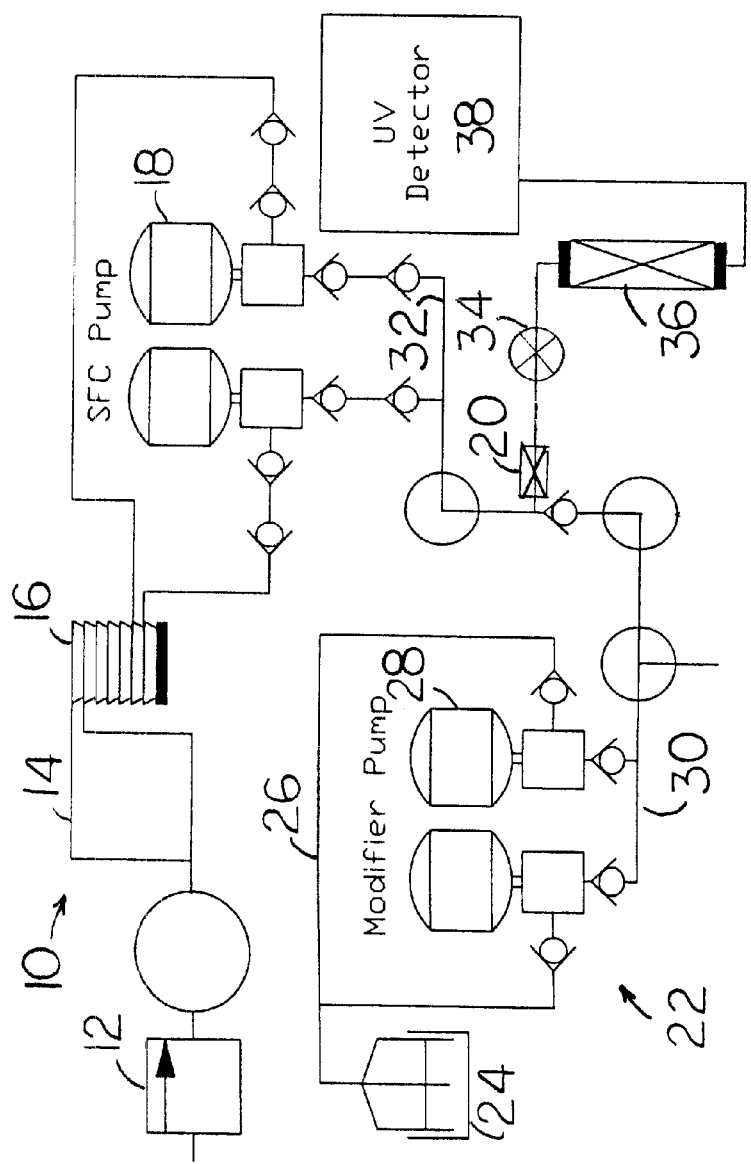
FIG. 1 is a flow chart of a supercritical fluid chromatography system.

An example of a supercritical fluid chromatography (SFC) system is illustrated in the schematic of FIG. 1. The system has a first flow stream 10 containing a highly compressed gas, compressible liquid or supercritical fluid, stored in a fluid supply tank 12. Liquefied compressed carbon dioxide (CO2) gas from a cylinder 12 is often used in SFC as the first flow stream. The CO2 passes through high-pressure stainless steel tubing 14 and a line chiller 16 that cools the fluid prior to entering supercritical fluid pumps 18. Supercritical fluid pumps 18 deliver high-pressure compressible fluid at or near supercritical levels to mixing column 20.

A second supply stream 22 adds a relatively incompressible liquid to the system. Methanol is often added as a solvent modifier to the mobile phase flow stream. Modifier liquid is drawn from a supply tank 24 through transfer tubing 26. Pumps 28, operating either alone or together in parallel, draw modifier from tank 24 and move the liquid at high pressure into the downstream mobile phase flow stream. The modifier flow stream 30 and highly compressed fluid 32 are combined together and then pass through a mixing column 20, creating a mixture of modifier dissolved into the supercritical fluid. A sample injection valve 34 is placed downstream of the mixing column. The sample prepared for separation is introduced injected into the mobile phase with an injection valve 34. After separation of sample components in the column 36, the elution mixture passes from the column outlet into a detector 38. From the detector 38, the sample components are captured by a collection system.

The method of the preferred embodiment resolves safety and operational hazards that occur during injections of samples into an SFC flow stream through an injection valve 34. To fully describe the present invention, a discussion of the problem solved by the invention is appropriate.

Figure 2:
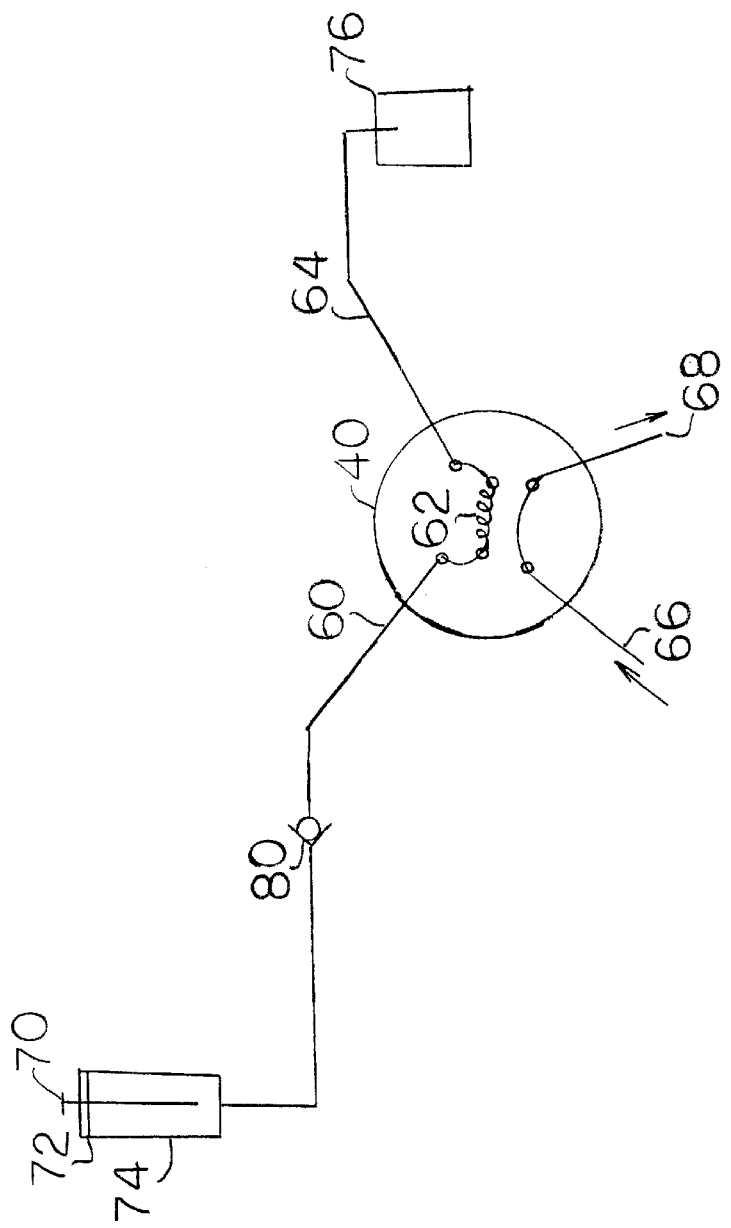
FIG. 2 is a diagram of an injection valve stator in the load position.
Figure 3:
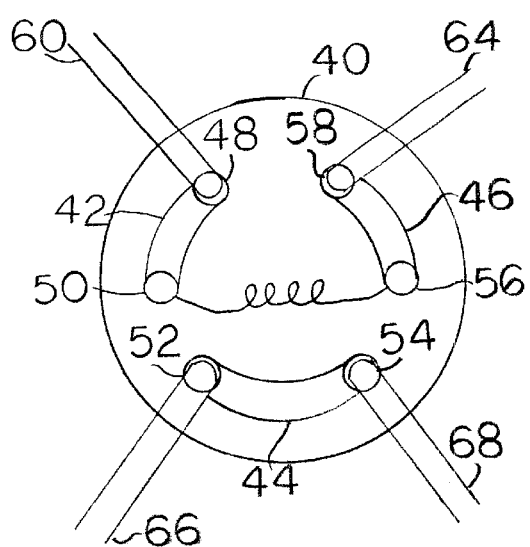
FIG. 3 is a diagram of an injection valve system of the preferred embodiment in the load position.

An injection valve works by receiving a measured volume of sample injected into a sample fill port with a syringe or syringe pump. Through the fill port, the sample liquid enters into a sample loop that may completely fill or remain partially fill of sample. Referring to FIGS. 2 and 3, when sample is added to the injection loop 62 of an injection valve 34, the sample liquid inside the loop 62 is at atmospheric pressure. When the sample is ready for injection, the valve 34 is set to inject position and the mobile phase flow stream flows through the loop 62, flushing out the sample into the flow stream. A channel 46 connects ports 54 and 56 and channel 44 connects ports 52 and 50. Sample inlet 60 is connected to waste line 64 through channel 42. The sample in loop 62, at low pressure, is brought inline with the mobile phase from 66 at high pressure. The flow 66 from the pumps 18 travels through the loop 62 and pushes the sample out of the loop into the mobile phase flow stream, which is methanol and CO2 in an exemplary embodiment, towards the column 36. While inline, the volumetric space of the loop becomes pressurized at the mobile phase pressures ranging from 100 to 600 bar.

Figure 5:
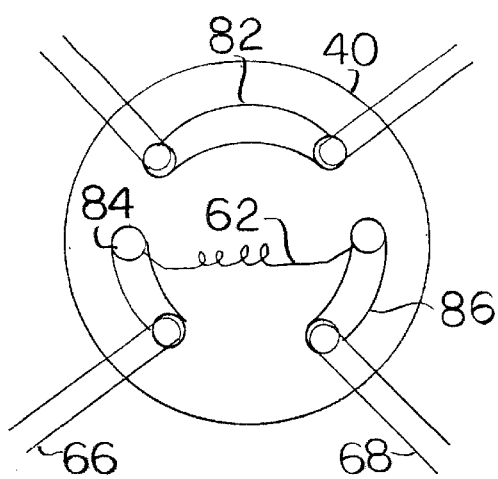
FIG. 5 is a diagram of an injection valve stator in the inject position.
Figure 4:
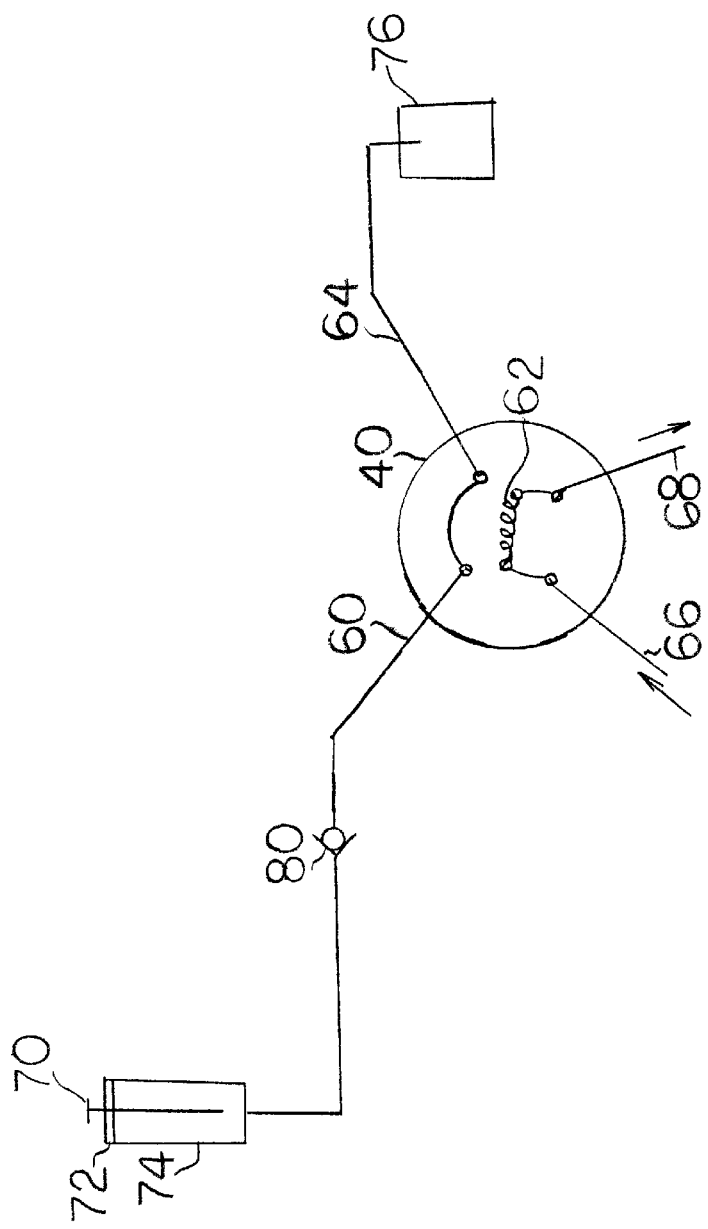
FIG. 4 is a diagram of an injection valve system of the preferred embodiment in the inject position.

Referring to FIG. 3, injection valve 34 rotates through a center axis and directs the sample according to whether the sample is loading into the valve, illustrated in FIG. 2, or injected into the flow stream, illustrated in FIG. 4. FIG. 3 is a diagram that illustrates a multi-port injection valve in a "Load" position. FIG. 5 is a diagram that illustrates the same injection valve in an "Inject" position. Three channels 42, 44, 46 are the flow paths in the valve, depending on status. The six holes 48–58 in the stator 40 represent ports. In the load position, mobile phase flows in flow path 66 through port 52, channel 44 and out port 54 to flow path 68 which leads to the column 36. A syringe 70 is passed through a septum 72 and injects sample through the sample port 74, into the injection valve 34 through flow stream 60 and port 48. The sample fills channel 42 and enters sample loop 62. The sample loop 62 is partially or completely filled with sample from a syringe. Overflow or displaced fluid from the sample loop 62 exits the injection valve through channel 46, and port 58 into a waste collection system 76.

After the sample is injected, valve 34 is reset to a load position inline with a sample fill port 74. However, high-pressure mobile phase that was flowing through the loop 62 becomes trapped in the sample loop 62. As the injection valve 34 rotates to the load position, the sample loop 62 comes into communication with the sample transfer line 60 through channel 42. When the valve 34 is reset to load, high-pressure mobile phase in the sample loop 62 is brought inline with the fill line 60 and quickly expands in a 500:1 ratio into the low-pressure zones in 60 up to sample port 74. This presents a serious safety hazard. Larger loop sizes of 0.1 to more than 100 mL can cause expansion volumes to reach one half to 50 liters of gas and aerosol. The expanding gas can exit the SFC system in an uncontrolled manner out of the fill port 74 and into the open air. The reaction places the laboratory personnel and sensitive laboratory equipment at risk from exposure to decompressed modifier solvent and mobile phase that contains hazardous substances.

A second hazard emanating from the expanding flow stream arises when laboratory personnel forget to remove a syringe 70 from a previous injection from the fill port 74 when the valve 34 is reset to the load position. Syringes are used in SFC to manually fill the injection valve loop. Syringes are not always removed properly from a fill port after filling an injection loop. The pressure from trapped mobile phase in an injection valve loop from a previous injection can blow a syringe out of the sample fill port and propel the sharp projectile at high velocity through the laboratory, creating an obvious safety hazard to personnel and equipment.

The present invention prevents and contains the expansion of mobile phase from an injection valve 34 that is reset from an "inject" position to a "load" position after injection of sample into an SFC flow stream. FIG. 2 illustrates a check valve 80 that is installed downstream from the sample port 74 and upstream of the injection valve 34 that allows flow from the syringe 70 into the sample loop 62 for refilling in the load position but prevents high-pressure blowback from the sample loop 62 after sample injection. Instead of expanding through fill line 60, high-pressure mobile phase is stopped by the check valve 80 and directed to a low-pressure waste collector 76 through port 58. The waste collection 76 is at a lower, or even atmospheric, pressure, and therefore the compressed mixture will expand into this system away from the sample port 74. The waste system 76 is a collection system of flow stream mixtures for disposal or recycling.

The present invention is a more efficient method of adding sample to an SFC system. Blocking the path to the fill port pressure forces in the sample loop towards the waste collector. The pressure inside the sample loop quickly dissipates to the waste stream 76. This process prepares the sample loop for a subsequent filling of sample without additional handling or time delays experienced attempting to manually release the pressure. After dispensation of the mobile phase to the waste collector 76, samples are added to the sample loop 62 in the valve quickly and efficiently after an injection into the mobile phase occurs.

Referring to FIG. 2, check valve 80 operates in an open flow position when sample from the syringe 70 fills loop 62 via transfer tube 60 and port 48. By placing a pressure stop between the loop 62 and sample port 74, the mobile phase trapped in loop 62 must expand into line 64 leading to low-pressure waste collection 76. The waste collection system 76 can be held at atmospheric pressure or an elevated pressure to exert greater control over the rate of mobile phase expansion out of the sample loop 62. After sample loop contents are collected in containment 76, the pressure against check valve 80 is dissipated as the pressure inside the loop 62 returns to atmospheric pressure. At atmospheric pressure, a new sample injection may be safely added with a syringe 70 into the loop 62. With the current invention in an SFC system, the danger of exposing operating personnel and laboratory equipment to uncontrolled releases of supercritical mobile phase and a high-velocity ejection of a syringe is greatly reduced.

The types of check valves used in the preferred embodiment may include any type of laboratory-grade check valve that is suited to operate within the elevated pressures in an SFC system. Examples are flange type safety check valves and traditional ball-and-seat type of valves. Both types of valves operate by remaining normally open and positioned such that the high-pressure blowback from a sample loop will force the valve to the closed position. Flange valves are normally constructed with stainless steel to protect against wear and chemical corrosion.

Ball-type check valves have a ball of a certain diameter that sits freely above a seat. The seat has a single through-hole with a diameter slightly smaller than that of the ball. Liquid and gas mixtures cannot pass through the check valve in any way but through the seat hole in the seat. When pressure from behind the seat is greater than the pressure above the ball, flow passes through the valve. However, when the pressure from flow above the ball is greater than the pressure behind the seat, the ball is forced against the seat, thereby forming a seal and preventing flow through the valve.

In the present invention, the check valve 80 is positioned to such that high-pressure gas and liquid mixtures that are displaced from the sample loop 62 in the injection valve 34 are above the ball, and low, or atmospheric, pressure is below the seat. Therefore, when the injection valve 34 is reset after injecting a sample, the release of high pressure towards the sample port 74 must pass through the check valve 80, and will force ball against the seat, thereby closing the check valve.

The present invention reduces a safety hazard not only to humans but also to the environment. The uncontrolled explosion of mobile phase out of the injection valve releases into the atmosphere as clouds of solvent aerosols and supercritical vapor. The present invention improves the environment by minimizing the risk of exposure to high-pressure mobile phase flow stream mixtures expanding into the open air atmosphere, which typically contain solvents combined with carbon dioxide, freon, or other compressible gasses.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed:

1. A method of sample introduction into a flow stream containing a mixture of highly compressed gas, compressible liquid or supercritical fluid, and a relatively incompressible liquid, comprising:
   preventing expansion of flow stream contents trapped within a sample loop of a multi-port injection valve into the environment through a sample fill port by placing a check valve between said sample loop and said fill port;
   directing said flow stream contents from said sample loop to a waste collection system.

2. The method of claim 1, wherein:
   said check valve is placed in a normally open position and closes when high-pressure flow stream mixtures from inside said injection apparatus are displaced towards a low pressure waste collector.

3. The method of claim 1, wherein:
   preventing expansion of said trapped flow stream contents comprises controlling displacement of the flow stream contents that become trapped within said sample loop after said sample is injected into said flow stream and said injection valve is reset to receive a second said sample, thereby preventing said high pressure flow stream contents from expanding out of said sample fill port and directing said flow stream contents towards a waste collection system.

4. The method of claim 1, further comprising:

controlling displacement of high-pressure contents trapped within a sample loop from said injection valve away from said fill port.

5. A method of sample introduction into a flow stream containing a mixture of highly compressed gas, compressible liquid or supercritical fluid, and a relatively incompressible liquid, comprising:

loading sample into an injection valve through a fill port;

injecting said sample into said flow stream;

resetting said injection valve to load a second sample;

controlling displacement of high-pressure flow stream contents trapped within said injection valve away from said fill port by placing a check valve between said fill port and said injection valve.

6. The method of claim 5, wherein:

said injection valve is a multi-port injection valve having a microliter sample loop.

7. A method of sample introduction into a flow stream containing a mixture of highly compressed gas, compressible liquid or supercritical fluid, and a relatively incompressible liquid, comprising:

loading sample into an injection valve through a fill port;

injecting said sample into said flow stream;

resetting said injection valve to load a second sample;

controlling displacement of high-pressure flow stream contents trapped within said injection valve away from said fill port by placing a check valve between said fill port and said injection valve;

placing said check valve in a normally open position and closing said check valve when the high-pressure flow stream trapped inside said injection valve is displaced towards said fill port.

8. The method of claim 5, wherein:

said high-pressure flow stream in said injection valve that is displaced away from said fill port by said check valve is directed towards a port connected to a low-pressure waste collection system.

9. A method of sample introduction into a flow stream containing a mixture of highly compressed gas, compressible liquid or supercritical fluid, and a relatively incompressible liquid, comprising: loading sample into an injection valve through a fill port; injecting said sample into said flow stream;

resetting said injection valve to load a second sample;

controlling displacement of high-pressure flow stream contents trapped within said injection valve away from said fill port by placing a check valve between said fill port and said injection valve; and controlling displacement of high-pressure contents trapped within a sample loop from said injection valve away from said fill port.

10. A method of sample introduction into a flow stream containing a mixture of highly compressed gas, compressible liquid or supercritical fluid, and a relatively incompressible liquid, comprising:

loading sample through a fill port and into an injection valve sample loop;

injecting said sample into said flow stream;

controlling displacement of high-pressure flow stream contents that become trapped within said sample loop after said sample is injected into said flow stream and said injection valve is reset to receive a second said sample by placing a check valve between said sample loop and said fill port, thereby preventing said high pressure flow stream contents from expanding out of said sample fill port and directing said flow stream contents towards a waste collection system.

11. The method of claim 10, wherein:

said high-pressure flow stream in said injection valve that is displaced away from said fill port by said check valve is directed towards a port connected to a low-pressure waste collection system.

12. The method of claim 10, wherein:

said check valve is placed in a normally open position and closes when high-pressure flow stream trapped inside said injection valve is displaced towards said fill port.

13. A method of sample introduction into a flow stream containing a mixture of highly compressed gas, compressible liquid or supercritical fluid, and a relatively incompressible liquid, comprising:

loading sample through a fill port and into an injection valve sample loop;

injecting said sample into said flow stream;

controlling displacement of high-pressure flow stream contents that become trapped within said sample loop after said sample is injected into said flow stream and said injection valve is reset to receive a second said sample by placing a check valve between said sample loop and said fill port, thereby preventing said high pressure flow stream contents from expanding out of said sample fill port and directing said flow stream contents towards a waste collection system;

controlling displacement of high-pressure contents trapped within a sample loop from said injection valve away from said fill port.

* * * * *